US008709404B2

(12) United States Patent
Winqvist et al.

(10) Patent No.: US 8,709,404 B2
(45) Date of Patent: *Apr. 29, 2014

(54) IMMUNOTHERAPY IN CANCER TREATMENT

(75) Inventors: Ola Winqvist, Uppsala (SE); Magnus Thörn, Uppsala (SE)

(73) Assignee: Sentoclone International AB, Stockholm (SE)

( * ) Notice: Subject to any disclaimer, the term of this patent is extended or adjusted under 35 U.S.C. 154(b) by 1605 days.

This patent is subject to a terminal disclaimer.

(21) Appl. No.: 10/530,738

(22) PCT Filed: Oct. 8, 2003

(86) PCT No.: PCT/SE03/01573
§ 371 (c)(1),
(2), (4) Date: Feb. 21, 2007

(87) PCT Pub. No.: WO2004/032951
PCT Pub. Date: Apr. 22, 2004

(65) Prior Publication Data
US 2007/0141026 A1 Jun. 21, 2007

(30) Foreign Application Priority Data
Oct. 11, 2002 (EP) .................................... 02022787

(51) Int. Cl.
*A01N 63/00* (2006.01)
(52) U.S. Cl.
USPC ...................................................... 424/93.71
(58) Field of Classification Search
None
See application file for complete search history.

(56) References Cited

U.S. PATENT DOCUMENTS

| | | | |
|---|---|---|---|
| 4,478,815 A | | 10/1984 | Burchlel et al. |
| 5,767,065 A | * | 6/1998 | Mosley et al. ................. 514/2 |
| 5,814,295 A | | 9/1998 | Martin et al. |
| 7,012,098 B2 | | 3/2006 | Manning et al. |
| 8,211,425 B2 | * | 7/2012 | Winqvist et al. ........... 424/93.71 |
| 2002/0182730 A1 | * | 12/2002 | Gruenberg ................. 435/375 |
| 2003/0129749 A1 | | 7/2003 | Gundersen et al. |
| 2003/0228635 A1 | * | 12/2003 | Hu et al. ..................... 435/7.2 |
| 2006/0104950 A1 | | 5/2006 | Okano et al. |
| 2009/0022695 A1 | | 1/2009 | Winqvist et al. |
| 2009/0074714 A1 | | 3/2009 | Winqvist et al. |
| 2009/0081175 A1 | | 3/2009 | Winqvist et al. |
| 2009/0123443 A1 | | 5/2009 | Winqvist et al. |
| 2009/0220472 A1 | | 9/2009 | Winqvist et al. |
| 2009/0297489 A1 | | 12/2009 | Winqvist et al. |
| 2010/0015161 A1 | | 1/2010 | Winqvist et al. |

FOREIGN PATENT DOCUMENTS

| | | | |
|---|---|---|---|
| EP | 645147 A1 | 3/1995 | |
| EP | 1408106 A1 | 4/2004 | |
| JP | 7-179352 | 7/1995 | |
| JP | 7-179352 A | 7/1995 | |
| JP | 2002-519019 A | 7/2002 | |
| WO | WO 97/46256 | 12/1997 | |
| WO | 99/53949 A | 10/1999 | |
| WO | 00/00587 A1 | 1/2000 | |
| WO | WO 01/05433 | * 1/2001 | ............. A61K 47/48 |
| WO | 2004/012681 A1 | 2/2004 | |
| WO | 2004/016154 A2 | 2/2004 | |
| WO | 2004/032951 A1 | 4/2004 | |
| WO | 2004/045650 A1 | 6/2004 | |

OTHER PUBLICATIONS

Janeway et al. (Immunobiology 5, Garland Science, 2001, Figure A.24).*
Janeway et al. (Immunobiology 5, Garland Science, 2001, Appendix III) t.*
Harada et al. (Immunology 1996 87: 447-453).*
Spits et al. (J. Immunology 1987 139: 1142-1147).*
Hofman et al. (J. Immunology 1988 141:1185-1190).*
Perussia et al. (J. of Immunology 1992 149: 3495-3502).*
Biron (Immunity 2001 14: 661-664).*
Byers, T. (CA Cancer J Clin. vol. 49, No. 6, Nov./Dec. 1999).*
Okamoto et al. (Cancer Immunol. and Immunotherap. 1995 40-173-181).*
National Cancer Institute (sentinel lymph node, www.cancer.gov, downloaded Jun. 12, 2009).*
Wedgewood Pharmacy (http://www.wedgewoodpharmacy.com/isosulfan/ 2004)).*
Meijer et al. (J. Clin. Pharmacol. Jul. 2001 441:81S-94S).*
Santin et al. (Am J. Obstet. Gynceol. Sep. 2000, 183: 601-609).*
Kan et al. (Biotherapy, 6:245-250 1994).*
Stratagene Catalog (1988, p. 39).*
Chin, C.S. et al., "Sentinel Node Mapping Identifies Vaccine-Draining Lymph Nodes with Tumor-Specific Immunological Activity," *Annals of Surgical Oncology* (2002); 9(1):94-103.
Lind, D.S. et al., "Expansion and tumour specific cytokine secretion of bryostatin-activated T-cells from cryopreserved axillary lymph nodes of breast cancer patients," *Surgical Oncology* (1993); 2:273-282.
Panelli, M.C. et al., "Expansion of Tumor-T Cell Pairs from Fine Needy Aspirates of Melanoma Metastases," *Journal of Immunology* (2000); 164(1):495-504.
Cochran et al. "Sentinel Lymph Nodes Show Profound Downregulation of Antigen-Presenting Cells of the Paracortex: Implications for Tumor Biology and Treatment." Mod. Phathol., (2001), 14(6):604-608.
Frisell et al. "Sentinel Node in Breast Cancer—a Swedish Pilot Study of 75 Patients." Eur. J. Surg. (2001) 167:179-183.
Leong et al. "Cytokine Profies of Sentinel Lymph Nodes Draining the Primary Melanona." (2002) 9(1):82-87.
Yamshchikov et al. "Evaluation of Peptide Vaccine Immunogenicity in Draining Lymph Nodes and Peripheral Blood of Melanoma Patients." Int. J. Cancer (2001) 92:703-711.
Elliott, T. et al., "Immunology Paper Alert", *Current Opinion in Immunology* (2001), 13:625-633.

(Continued)

*Primary Examiner* — Peter J Reddig
(74) *Attorney, Agent, or Firm* — Porter Wright Morris & Arthur LLP

(57) ABSTRACT

The present invention relates to a novel method of cancer immuno-therapy and to a kit for use in this method. Specifically, the present invention relates to a novel method of collecting lymphocytes from sentinel lumph nodes and in vitro culture for the multiplication thereof lymphocytes.

14 Claims, 6 Drawing Sheets

(56) References Cited

OTHER PUBLICATIONS

Marits, P. et al., "Sentinel node lymphocytes: tumour reactive lymphocytes identified intraoperatively for the use in immunotherapy of colon cancer," *British Journal of Cancer* (2006), 94(10):1478-1484.
Tanis, Pieter J. et al., "History of sentinel node and validation of the technique", *Breast Cancer Research* (2001), 3:109-112.
Burnet, Prog Exp Tumor Res, 13:1-27 (1970).
Ratliff, J. Urol., 137(1):155-158 (1987).
Ratliff, J. Urol., 150(3):1018-1023 (1993).
Cohen et al, Urol Clin North Am, 19(3):421-428 (1992).
Tanaka et al, J. Immunotherapy, 25(3):207-217 (2002).
Mesel-Lemoine et al, Blood, 107(1):381-388 (2006).
Zhou et al, Blood, 107(2):628-636 (2006).
Sakaguchi, Nature Immunology, 6(4):345-352 (Apr. 2005).
Moore, Clinically Oriented Anatomy, Baltimore: Williams & Wilkins, 1985, pp. 41-46.
Renkin, Am J Physiology, H706-H710 (1986).
35th Annual Meeting and 20th Summer School of the Scandinavian Society for Immunology, Aarhus, Denmark, Jun. 13-16, 2004, Scandinavian Journal of Immunology, 59(6):609-637 (Jun. 2004).
Chen et al, J. Experimental Medicine, 198:1875-1886 (2003).
Kursar et al, J. Experimental Medicine, 196:1585-1592 (2002).
Sutmuller et al, J. Experimental Medicine, 194:823-832 (2001).
Dahl, European Journal of Surgical Oncology, 31:381-385 (Jan. 28, 2005).
Saxton et al, Blood, 89:2529-2536 (1997).
Rosenberg et al, Journal of the National Cancer Institute, 85(8):622-632 (1993).
Winter et al, Immunology, 108:409-419 (2003).
Rosenberg et al, Proceedings of the National Academy of Sciences, USA, 101:14639-14645 (2004).
Ruttinger et al, Clinical and Experimental Metastasis, 21:305-312 (2004).
Kim et al, Cancer, 86:22-30 (1999).
Hedfords et al, Scandinavian Journal of Immunology, 58:522-532 (2003).
Dillmon, Expert Review of Anti-Cancer Therapy, 5(6):1041, Abstract (2005).
Dudley et al, Nature Reviews Cancer, 3:666-675 (2003).
Marincola et al, Trends in Immunology, 24(6):334-341 (2003).
Gura, Science, 278:1041-1042 (1997).
Kaiser, Science, 31:1370 (2006).
Bowie et al, Science, 257:1306-1310 (1990).
Rudikoff et al, PNAS USA, 79:1979-1983 (1982).
Coleman et al, Research in Immunology, 145(1):33-36 (1994).
Burgess et al, Journal of Cell Biology, 111:2129-2138 (1990).
George et al, Trends in Immunology, 26(12):653-659 (2005).
Thorn et al, Cancer Causes control, 8(4):560-567 (1997).
Holmang et al, J. Urol. 158(2):389-392 (1997).
Sternberg, Annals of Oncology, 13:273-279 (2002).
Advanced Bladder Cancer Meta-Analysis Collaboration, Lancet, 361:1927-1934 (2003).
Bassi et al, J. Urol., 161(5):1494-7 (1999).
Cabanas, Cancer, 39:456-466 (1977).
Balch et al, J. Clin. Oncol., 19:3622-3634 (2001).
Sherif et al. et al, J. Urol., 166(3):812-815 (2001).
Lipponen et al, Eur. J. Cancer, 29A(1):69-75 (1992).
Morales et al, J. Urol., 116(2):180-183 (1976).
Itano et al, Nature Immunology, 4:733-739 (2003).
Moll et al, Am. J. Pathol., 140(2):427-447 (1992).
Ochsenbein et al, Nature, 411:1058-64 (2001).
Velotti et al, J. Immunotherapy, 20(6):470-478 (1997).
Baner et al, Clin Chem, 51(4):768-775 (2005).
Haas et al, Cancer Immunol Immunother, 30(6):342-350 (1990).
Housseau et al, Int J Cancer, 71(4):585-594 (1997).
Dudley et al, J. Clin. Oncol., 23(10):2346-2357 (2005).
Nakagomi et al, Cancer Res, 53:5610-5612 (1993).
Finke et al, Cancer Res, 53(23):5613-5616 (1993).
Martis et al, European Urology, 49(14):59-70 (Nov. 14, 2005).
Sherif et al, European Urology, 50(1):83-91 (Jul. 2006).
Farzad, Z. et al., "Lymphocytes from lymph nodes at different distances from human melanoma vary in their capacity to inhibit/enhance tumor cell growth in vitro", *Melanoma Research*, (1997), 7(2):S59-S65.
*Proceedings of the American Association for Cancer Research*, (2001), 42:683-684.

\* cited by examiner

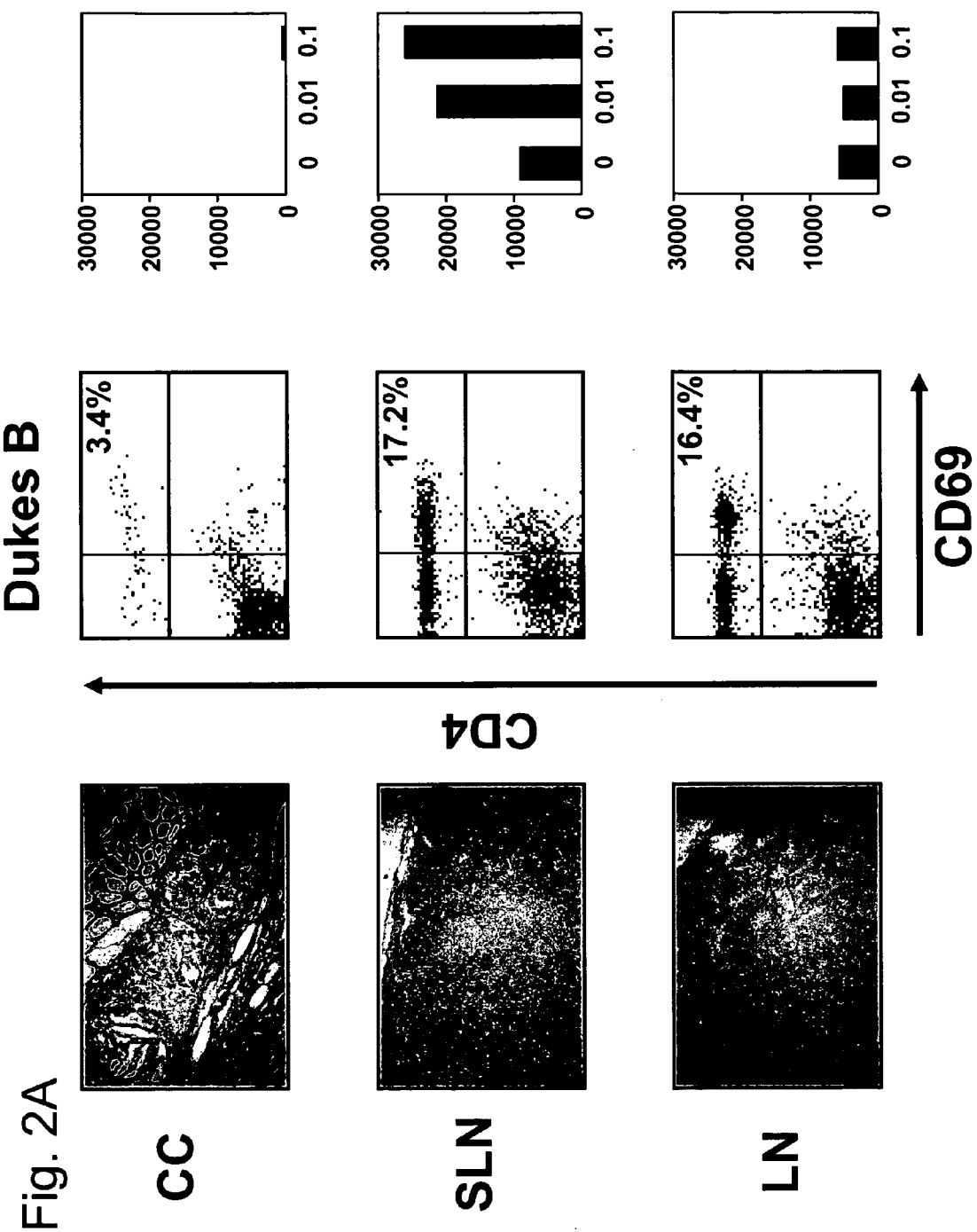

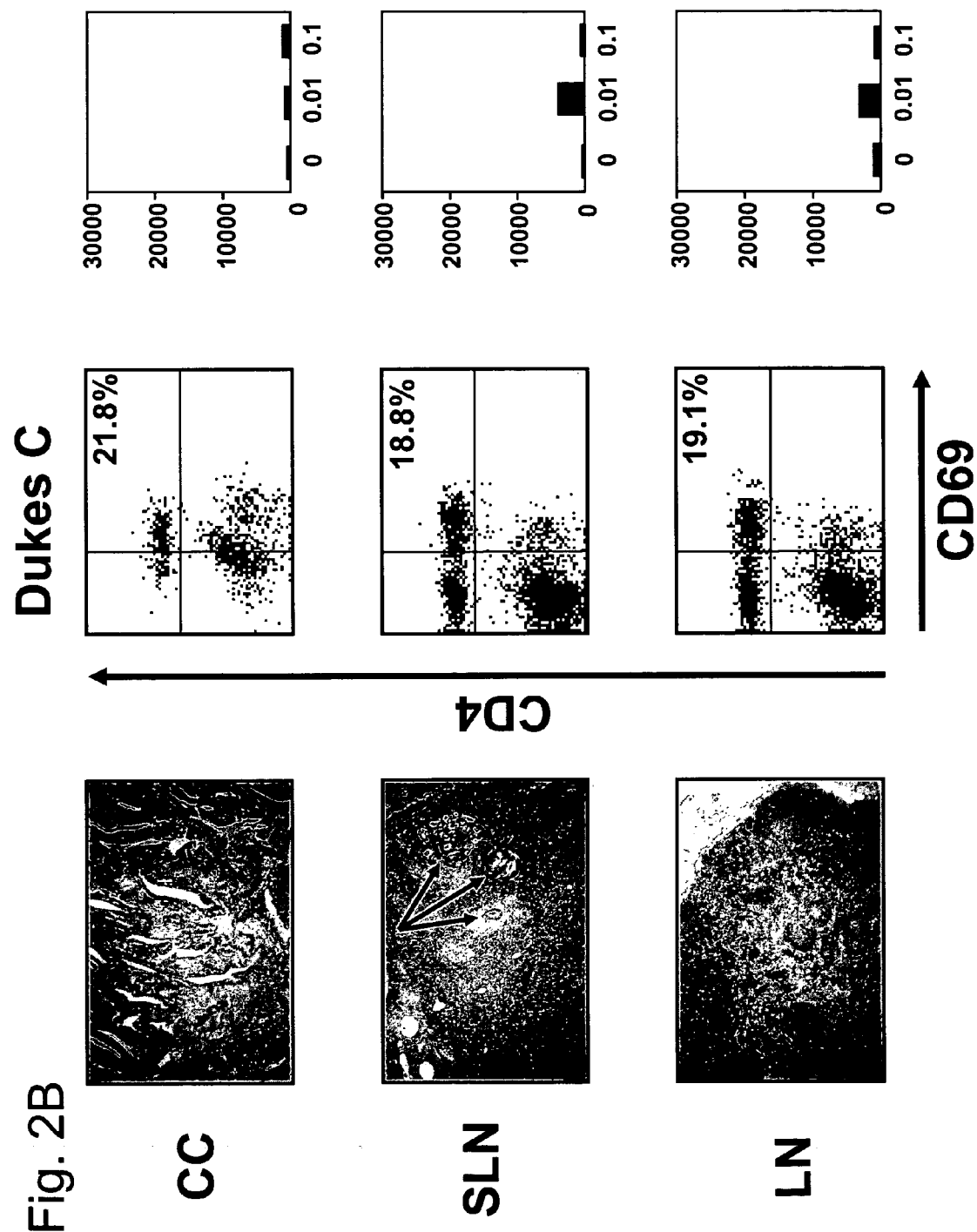

Presence of lymph node metastasis supress activation of T-lymphocytes

IMMUNOTHERAPY IN CANCER TREATMENT

CROSS REFERENCE TO RELATED APPLICATIONS

This application is a national phase filing under 35 U.S.C. §371 of international application number PCT/SE2003/001573, filed Oct. 8, 2003, which claims the benefit of priority of European application number 02022787.2, filed Oct. 11, 2002. The disclosures of the prior applications are considered part of (and are incorporated by reference in) the disclosure of this application.

The present invention relates to a novel and improved method of cancer immuno-therapy and to a kit for use in this method. Specifically, the present invention relates to a method of providing lymphocytes obtained from sentinel lymph nodes of a cancer patient and expanding them in vitro.

Cancer, a term frequently used to indicate any of the various types of malignant neoplasms, is one of the leading causes of death in humans. At present, cancer accounts for approximately 23% of all deaths in the world, with only cardiovascular diseases claiming more lives. During the lifetime of an individual cancer may develop in any tissue of any organ and at any age with the transformed cells invading surrounding tissues or metastasizing to several sites in the body. At present there is growing evidence that apart from endogenous factors also certain activities and environmental conditions, such as smoking, exposure to specific compounds contained in food or released by industrial processes account for the development of and enhance the risk for certain types of cancers and tumors.

Once cancer has been diagnosed, treatment decisions become paramount. In the past, both local and regional therapies have been applied, specifically surgery and/or radiation, which are usually combined with systemic therapy, i.e. administration of anti-neoplastic drugs.

Surgery is the oldest form of cancer therapy, but suffers from various shortcomings. It will be successful only, if the tumor is detected in an early developmental stage, at which cells of the primary tumor have not started to disseminate yet, and the treatment success varies greatly between the cancer sites. Radiation is utilized in addition to surgery or alone in cases, where the primary tumor is difficult to access by surgical means, such as in nodular and diffuse non-Hodgkin's lymphomas, squamous cell carcinoma of the head and neck, mediastinal germ-cell tumors, prostate cancer, or early stage breast cancer.

Along with any of these above two treatment regimen anti-neoplastic drugs are administered to a cancer patient, which are to prevent cell division or spread of neoplastic cells (chemotherapeutic treatment). Even though these agents are toxic for essentially all fast proliferating cells, in the adjuvant setting, chemotherapy may bring about a limited improvement reducing mortality, e.g. in colon cancer from 51% to 40% after more than five years of follow up.

Recently, two additional treatment regimes have been developed, the photodynamic therapy and tumor immuno-therapy.

In photodynamic therapy, photosensitizing compounds and lasers are utilized to produce tumor necrosis. Tumor localizing photosensitizing compounds are systemically administered to a patient and subsequently activated by a laser. Upon absorbing light of the appropriate wavelength the sensitizer is converted to an excited state, with cytotoxicity being mediated by the interaction between the sensitizer and molecular oxygen within the tissue treated to generate cytotoxic singlet oxygen.

Tumor immuno-therapy on the other hand tries to take benefit from the inherent task the immune system fulfils in the individual as an instrument for preserving the physical integrity of the body.

In principle, the mammalian immune system has two general mechanisms to protect the body, the non-specific or innate immune response and the specific or acquired immune response. In contrast to the innate response, which un-specifically combats any foreign invading material, the specific response is tailored to a particular substance (antigen), which is effected by clonal selection. Acquired immunity is mediated by specialized cells, the B-cells, that produce antibodies as effector molecules (implementing the humoral immune response), and T-cells that mediate their effectivity through the cell as such (cell mediated immunity).

The cells of the specific immune system generically combat and destroy each entity that has been recognized as not belonging to the body, i.e. as foreign or "non-self", while at the same time desisting from any attack to substances/antigens that are known to determine "self". Thus, any exogenous biological and non-biological entity entering/invading the individual's body, is attacked, but also any endogeneous matter, the immune system never has learnt about to represent "self" and recognizes as foreign.

In an individual the immune system usually provides an immunologic surveillance and prevents the development of cancer. Cancer immunity is mediated mainly by T-cells and NK cells, wherein transformed tumor cells are destroyed after being recognized as (tumor-associated) foreign material. i.e. antigens that are not known as belonging to "self" (T cells) or from lack of MHC class I expression (NK cells).

Medicine tried to exploit these mechanisms in cancer treatment and so far, two general methods have been applied in tumor immuno-therapy. According to a first method the innate immune response is stimulated by administering substances to tumor patients, such as interleukin-2, tumor necrosis factor or interferon. However, this approach did not prove to be quite successful, while showing strong side effects due to the high toxicity the administered substances show at the effective concentrations.

Another focus has been on the specific immune system, taking advantage of the immune system's endogenous capability to distinguish between "self" and "non-self". Generally the immune system attacks transformed cells, since they exhibit antigens recognized to be foreign or "non-self". However, in some instances tumor cells may escape the immune system in vivo, partly because the tumor associated antigen is not capable to elicit an immune response, or is not capable to effect a sufficient stimulation of T-cells, or for the reason that the tumor cells produce factors that down-regulate the immune response in vivo.

In order to assist the immune system in performing its endogeneous task mononuclear cells of a cancer patient have been isolated from peripheral blood and transferred into a culture, where they have been stimulated and expanded. After expansion they were infused back to the patient, however, giving success response rates of only up to 35%. One of the drawbacks resides in that peripheral blood contains only small numbers of lymphocytes with functioning activity against tumor antigens.

In order to overcome this deficiency a variation of such a procedure has been proposed, which includes isolating and expanding populations of lymphocytes that have infiltrated tumors in vivo, so-called tumor-infiltrating lymphocytes. Yet, this process suffers from the disadvantage of requiring a specific type of lymphocytes, which are present only in a rather late stage of tumor development and in low numbers. Furthermore, the tumor infiltrating lymphocytes are subjected to immunosuppressive substances from the tumor and finally the isolation of such lymphocytes is not always an easy task to achieve.

Therefore, a problem of the present invention resides in overcoming the above disadvantages of the prior art and providing a novel and improved method for immuno-therapy This problem has been solved by a method for treating and/or preventing the recurrence of cancer comprising the steps of providing lymphocytes obtained from sentinel lymph nodes and activating and expanding the lymphocytes thus obtained in vitro.

In the figures,

FIGS. 2A-2B show the results obtained from a characterization of lymphocytes.

Figure 1A:
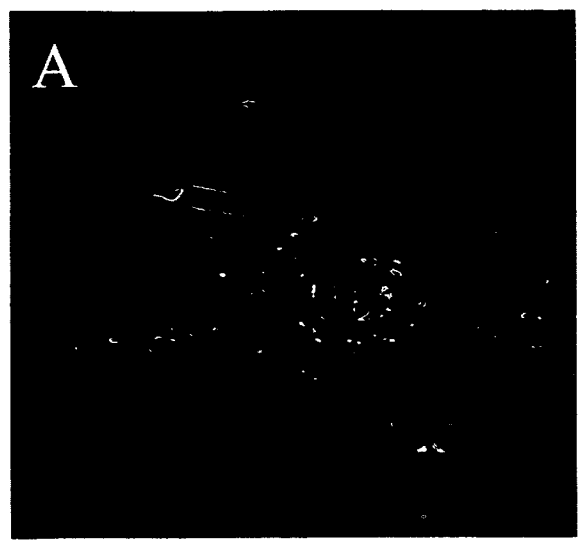
FIGS. 1A-1C show the results of a peroperative identification of sentinel node(s).

During the extensive studies leading to the present invention the inventors analyzed the immune profile of patients suffering from colorectal cancer and surprisingly found that even though lymphocytes isolated from peripheral blood or generically from the lymph system of the patients were unresponsive towards the tumor, sentinel lymph nodes of said patients harbor lymphocytes showing activity against tumor cells. Based on this finding the invention was accomplished, and a useful tool in cellular immuno-therapy is provided.

When carrying out the method as disclosed herein, first the sentinel nodes have to be located. Sentinel lymph nodes are generically defined as the first lymph node(s) in the lymphatic system that receive(s) lymphatic drainage from a primary tumor area. This may conveniently be achieved during surgery of the primary tumor(s), e.g. by introducing a tracer substance around or in the circumference of the tumor site, preferably prior to the surgical removal of the primary tumor. The tracer is transported in the lymph capillaries and accumulates via, phagocytosis by macrophages in the lymph nodes located downstream. Usually, the sentinel lymph nodes may be determined visually some minutes after applying the tracer substance by checking for lymph nodes coloured first or more intense.

As a tracer substance e.g. patent blue dye, lymphazurine blue or 99 Tc labelled albumin may be utilized.

Once the sentinel lymph nodes have been identified, they are isolated by surgical means and the histological status thereof may be assessed in representative slices from the nodes.

In a next step lymphocytes present in the remaining sentinel node material are collected and transferred to an in vitro culture. This may e.g. be achieved by pressing the lymph nodes so that they release their content with our without the presence of collagenase.

The cells thus obtained are subsequently subjected to an in vitro culture.

In case of removing unwanted cells from the culture and/or selecting for a specific sub-population of T-cells, e.g. CD4, CD8, CD69, CD62L positive or negative selection techniques may be applied, such as antibodies directed to surface markers unique to the cells selected. An example for such techniques is magnetic immuno-adherence wherein monoclonal antibodies directed to cell surface markers present on the cells to be selected are bound to a carrier. Selection of cells can also be achieved by flow cytometry assisted cell sorting under sterile conditions.

The cells may be cultured under conventional conditions in any medium suitable for growing lymphocytes cells including a Minimal Essential Media or RPMI Media 1640. In order to promote growth of the cells, factors necessary for proliferation and viability thereof may be added, including serum, e.g. fetal calf serum or human serum and antibiotics, e.g., penicillin streptomycin. The lymphocytes are maintained under conditions necessary to support growth, e.g. an appropriate temperature of around 37° C. and an atmosphere, e.g. air plus 5% $CO_2$.

During culture the lymphocytes are exposed to stimulating agents for expansion and optionally also to additional activation signals.

Expansion of lymphocytes may be achieved by contacting the cells with anti-CD3 antibodies, or contacting them with a protein kinase C activator (phorbol ester) in conjunction with a calcium ionophore. For a stimulation of an accessory molecule on the surface of the T-cells, a ligand which binds the accessory molecule may be employed. For example, T cells can be activated with an anti-CD3 antibody and an anti-CD28 antibody, under conditions appropriate for stimulating proliferation of the T-cells.

The primary and the co-stimulatory signal may be provided by different protocols. For example, the agents providing each signal can be in solution or coupled to a solid phase surface, e.g. the culture container. When coupled to a solid phase surface, the agents can be coupled to the same solid phase surface (i.e., in "cis" formation) or to separate surfaces (i.e., in "trans" formation). Also, one agent can be coupled to a solid phase surface and the other agent in solution.

To maintain long term stimulation of a population of T-cells following stimulation, the T-cells are subsequently separated from the stimulus. Yet, the T-cells may be maintained in contact with the co-stimulatory ligand throughout the culture term. The rate of T-cell proliferation is monitored periodically (e.g., daily) by, for example, examining the size or measuring the volume of the T-cells. When the mean T-cell diameter decreases after a peak they are reactivated and restimulated to induce further proliferation. Alternatively, the rate of T-cell proliferation and time for T-cell restimulation can be monitored by assaying for the presence of cell surface molecules, such as CD25, CD69, CD62L and MHC class II which are modulated on activated T-cells. For inducing long term stimulation of a population of CD4 or CD8 T-cells, it may be necessary to reactivate and restimulate the T-cells with a anti-CD3 antibody and an anti-CD28 antibody several times.

In addition, the T-cells obtained from the sentinel lymph nodes may be stimulated by the addition of cytokines, such as IL-2 for maintenance and expansion and IL-12, INF-α, and anti IL-4 antibody in order to activate CD4+ T helper cells towards IFN-γ producing Th1 effector cells. The amount of cytokine that should be added to the T-cell culture to obtain expansion to a sufficient extent may easily be determined by the skilled person. The cytokine is added from the first day of the culture, and added every other day of the culture in amounts sufficient to maintain proliferation of the T-cells.

E.g., IL-2 can be added to the cultures to obtain a final concentration of about 100 U/ml and is added every other day to the culture, such as every second or third day, when new medium is added to the cell culture.

Since according to the method of the present invention lymphocytes are utilized, that have been primed already in vivo and have a specificity against tumor antigens, no additional activation/priming is required in principle, since clonal expansion has already has occurred.

However, in patients with tumors producing immuno-suppressive substances the lymphocyte culture may be stimulated with tumor antigen in a form suitable to trigger an additional activation signal in the T-cells, i.e., the antigen is presented to the T-cell such that a signal is triggered in the T-cell through the TCR/CD3 complex. For example, the antigen can be presented to the T-cell by an antigen presenting cell, such as a B-cell, macrophage, monocyte, dendritic cell, Langerhans cell in conjunction with an MHC molecule. To this end, tumor cells, an autologous tumor extract and/or a recombinant tumor antigen are added to the culture of lymphocytes and incubated for a time sufficient for additional priming. Similarly, a cell infected with a pathogen, e.g., a virus, which presents antigens of the pathogen can be incubated with the lymphocytes. Following antigen specific activation of a population of T-cells, the cells can be further expanded according to the methods described herein. In view of patient safety use of an autologous tumor extract is preferred, since the step of removing tumor cells and or recombinant cells may be omitted.

It has further been found that when tumor cells are present in the sentinel lymph nodes the lymphocytes obtained therefrom exhibit a lower activity and/or specificity against the tumor cells as compared to lymphocytes obtained from tumor cell free sentinel lymph node. Without wishing to be bound by any theory it is presently believed that this finding is likely due to the tumor's capability of immuno-suppression, i.e. a functional state of anergy due to the presence of tumor cells.

When the lymphocyte culture has been expanded and stimulated to an extent desired, the lymphocytes are collected, optionally purged from any material, detrimental to the patient's health and transferred back into the patient. This may be achieved by intravenous infusion, during a period of from about 1 to 6 hours, with the number of mononuclear cells administered being dependent solely on the number of cells generated during the proliferation step.

According to another embodiment the present invention also provides a kit for carrying out the present method. The kit comprises a dye, preferably patent blue dye and agents for stimulating proliferation and expansion of lymphocytes.

The method of the present invention provides clear advantages over the prior art. Since the lymphocytes are collected from sentinel lymph nodes, specifically those lymphocytes are expanded that already have an activity and specificity directed against tumor antigens. This specificity may be enhanced in vitro, by culturing the lymphocytes in the presence of an autologous tumor extract to promote clonal selection and expansion. T-cells with specific reactivity towards the primary tumor can be identified in sentinel nodes and these cells can be expanded specifically for later use in cellular immuno-therapy.

The invention will now be explained by the following example that is not to be construed to be limiting but are given for illustrative purpose only.

EXAMPLE 1

Collection and Preparation of Cells

Five patients with colon cancer, with no signs of distant metastases or lymph node involvement prior to surgery, were included in the study (Table 1). The study was approved by the local ethical committee and informed consent was given by the patients.

The colonic tumor site was mobilized through division of peritoneal adhesions to facilitate inspection. One ml Patent blue dye (Guerbet, Paris) was injected superficially in the circumference of the tumor. Within five minutes, one to three blue-coloured mesenteric lymph nodes were identified macroscopically as sentinel nodes and they were marked with sutures.

The sentinel and non-sentinel nodes were cut in half. Slices less than 1 mm thick were cut from the central and the peripheral part of the nodes for flow cytometry and proliferation analysis. The rest of the node underwent routine histopathological examination. Tumors were histopathologically classified as Dukes stages A-C (11) (Table 1).

One piece of the primary tumor (including part of the invasive margin) was removed for flow cytometry analyses and as an antigen source.

Venous blood, sentinel and non-sentinel lymph nodes and tumors were immediately taken care of to minimize handling time. Peripheral blood leukocytes (PBL) where purified by ficoll-hypaque (Pharmacia, Amersham). Single cell suspensions of lymph node cells were obtained by gentle pressure using a loose fit glass homogenizer. Cells were resuspended and washed twice in DMEM containing 2.5% fetal calf serum (FCS) (Life technologies). Finally, cells were resuspended in RPMI proliferation media containing 10% human AB serum (Sigma), 1% penicillin-streptomycin (Sigma) and 1% glutamin (Sigma).

Tumor samples were homogenized using a Dounce homogenizer in 5 volumes (w/v) of phosphate buffered saline (PBS) followed by 5 minutes denaturation at 97° C. No intact cells were visible under the microscope. Tumor homogenates were diluted 1:10 and 1:100 in complete proliferation media. Purified PBL and lymph node cells were used at $3\times10^5$ cells/well in a proliferation assay against diluted tumor homogenate, concanavalin A 10 µg/ml (Sigma) or carcinoembryonic antigen 100 µg/ml (Sigma) in triplicate. Proliferation was measured on day 5, 6 and 7 by adding 1 µCi of $^3$H-Thymidine/well (Amersham) 16 hours prior to harvesting. Samples were subjected to scintillation counting.

PBL, lymph node cells and tumor cell suspensions at $1\times10^6$ cells/sample were subjected to investigation using flow cytometry (FACS). Cells were washed in PBS containing 2% FCS and 0.02% $NaN_3$ (FACS buffer) and directly triple labeled using fluorescent cell surface markers against CD4 PE, CD8 PerCp and the very early activation marker CD 69 FITC (Pharmingen). For intracellular FACS, cells were permeabilized with 0.3% saponin (Sigma) in FACS buffer for 15 minutes at room temperature followed by a 30 minute incubation with cytokeratin-20 antibody (Dakopatts). After washes, cells were incubated with an anti-mouse IgG FITC (Jackson) conjugated antibody for 30 minutes. Cells stained without the primary antibody were used as controls. After the staining, cells were investigated using a FACSscan (Becton Dickinson) and data was analyzed using the cellquest computer software (Becton Dickinson).

TABLE 1

Patient characteristics, locations of tumors, staging, investigated lymph nodes and proliferative responses.

| Patient | Sex | Age | Tumor site | Dukes classification | Positive nodes/ Harvest nodes | Mean CPM proliferation |
|---|---|---|---|---|---|---|
| 1. | F | 58 | Ascending | B | 0/29 | 15125[a] |
| 2. | F | 75 | Ascending | C | 4/23 | 3848[a] |
| 3. | F | 78 | Ascending | C | 2/19 | 78 |
| 4. | M | 81 | Ascending | B | 0/22 | 7686 |
| 5. | M | 80 | Sigmoid | B | 0/18 | 26289 |

[a]Peak at day 6 of mean proliferate responses where seen at tumor extract dilution 1/100

EXAMPLE 2

Peroperative Identification of Sentinel Node and Pathological Classification

Figure 1B:
Figure 1C:
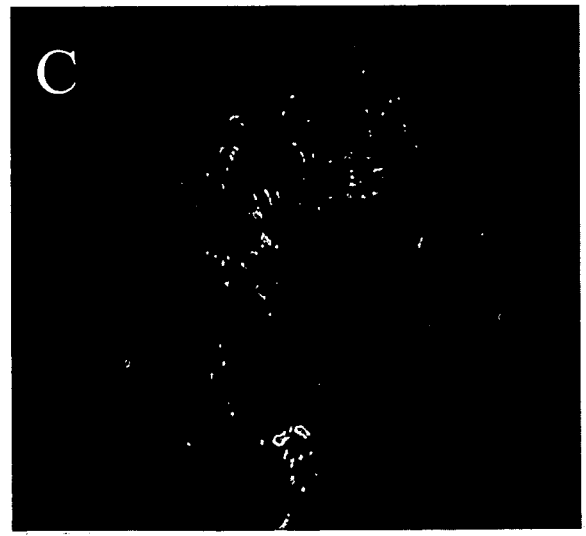

One to three sentinel nodes were detected intraoperatively using Patent blue injection in the circumference of the tumor (FIG. 1). Patient characteristics and location of the tumors are presented in table 1. Upon macroscopical dissection of the removed specimens, between 18 and 29 lymph nodes (average 22) were identified and embedded for histopathological evaluation (FIG. 2A, B left panels). Patients 2 and 3 (Table 1) had metastatic spread to the sentinel node and were histopathologically classified as Dukes C (FIG. 2B left panel). The other 3 patients did not show any signs of metastatic spread to sentinel node(s) nor to other lymph nodes despite tumors grew through the bowel muscular wall (FIG. 2A left panel). They were classified as Dukes B.

Single cell suspensions of lymphocytes collected separately from peripheral blood (PBL) (not shown), the tumor, draining sentinel lymph nodes and non-draining lymph nodes were triple stained with antibodies recognizing the very early activation marker CD69 and the T-cell markers CD4 (FIG. 2A, B middle panel) and CD8 (not shown) followed by flow cytometry analyses (FACS). Similar numbers of activated CD4$^+$ lymphocytes where found both in sentinel and non-sentinel nodes regardless of presence (FIG. 2A middle panel) or absence of metastases (FIG. 2B middle panel). All investigated tumors contained tumor infiltrating lymphocytes (TILs) to a various extent and the majority of these TILs, which were both CD4$^+$ and CD8$^+$ T-cells, presented and activated CD69$^+$ phenotype. In peripheral blood activated CD4$^+$CD69$^+$ lymphocytes were absent (not shown).

Figures 3A, 3B:
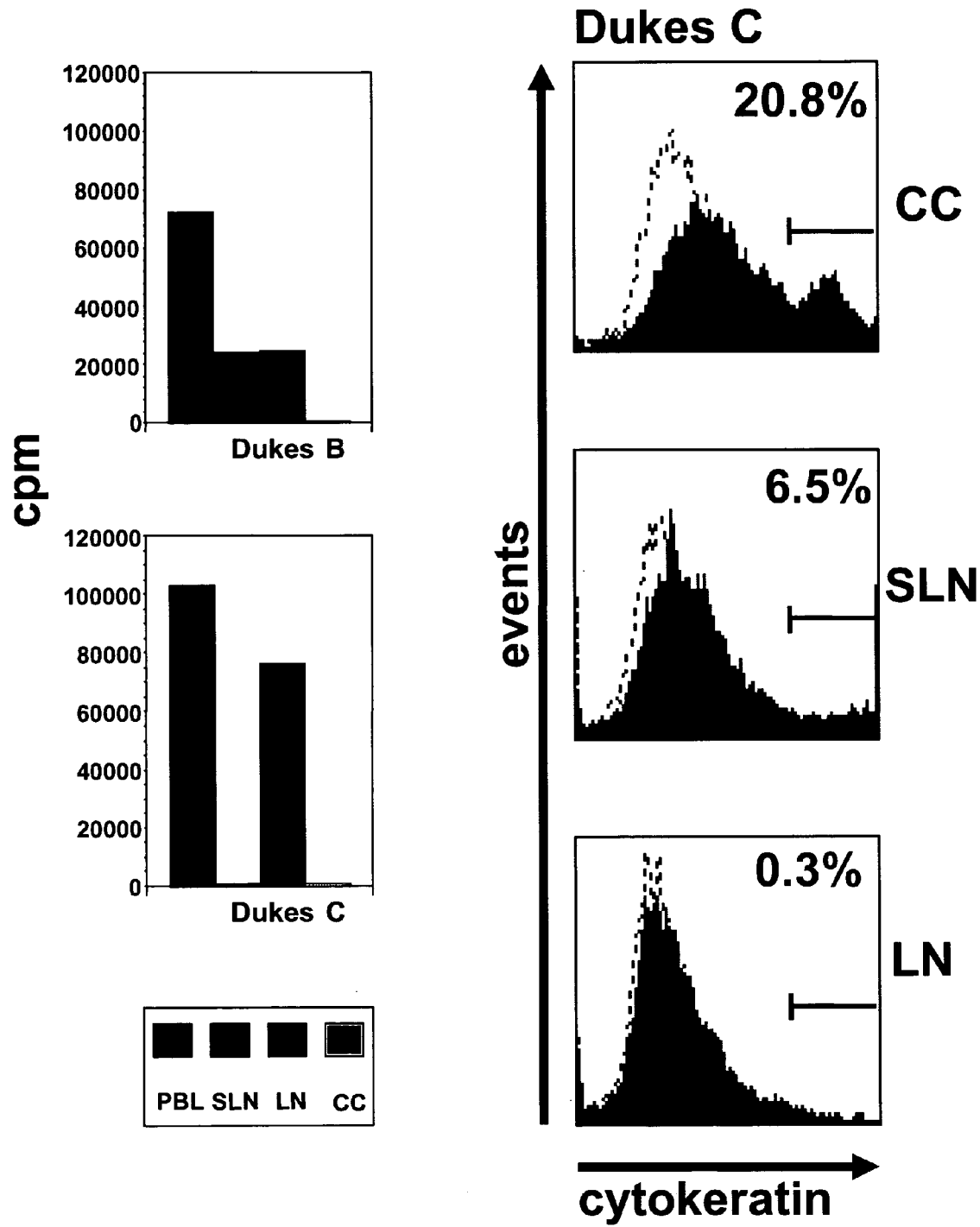
FIGS. 3A-3B show the results of an unspecific activation and intracellular FACS analyses for metastasis.
Figure 4A:
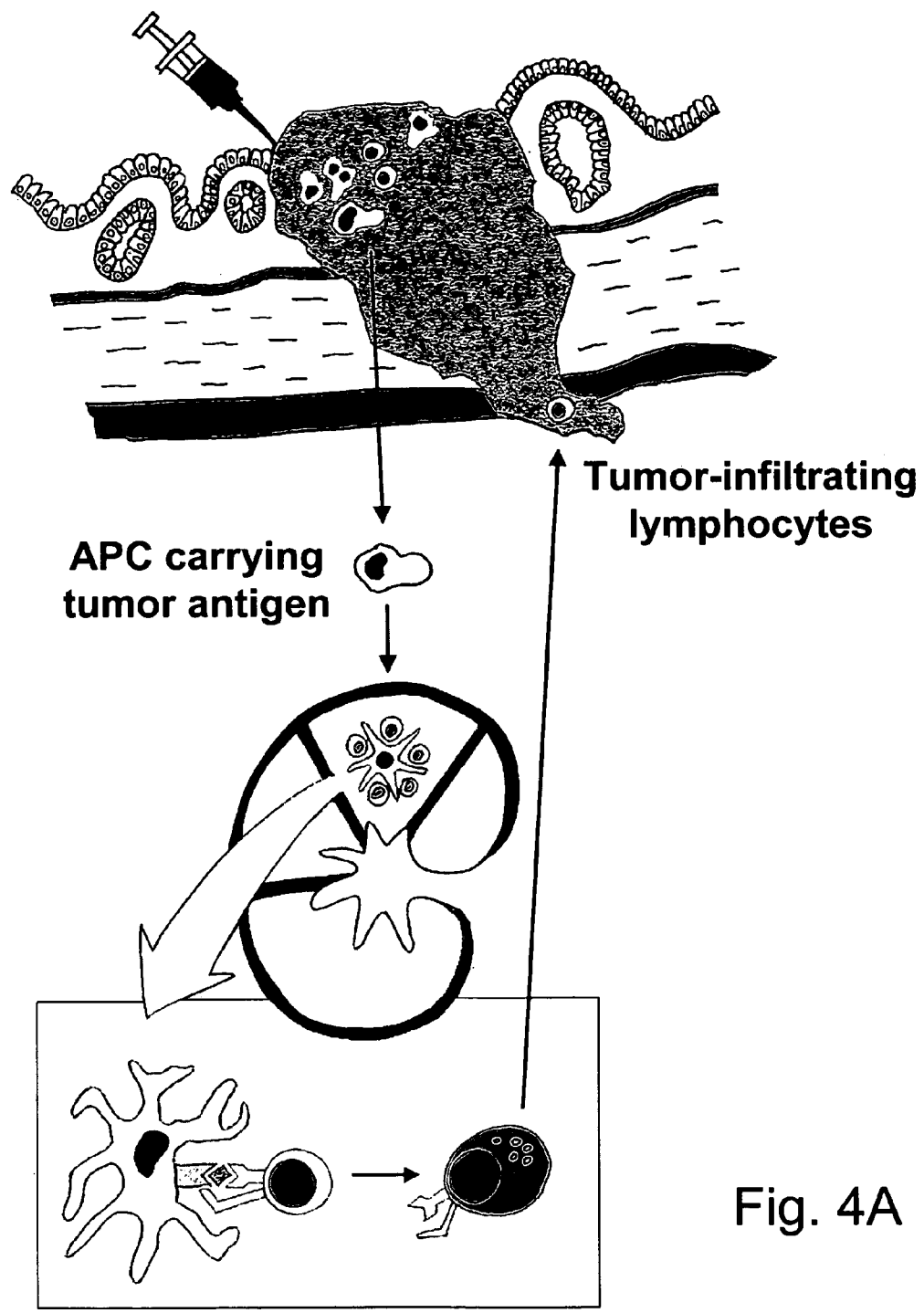
FIGS. 4A-4B show a hypothetical scheme of how antigenic material from the tumor is transported by the lymph vessels to the draining lymph node, identified by tracer dye, where presentation of antigenic peptides and activation of T cells occur.
Figure 4B:
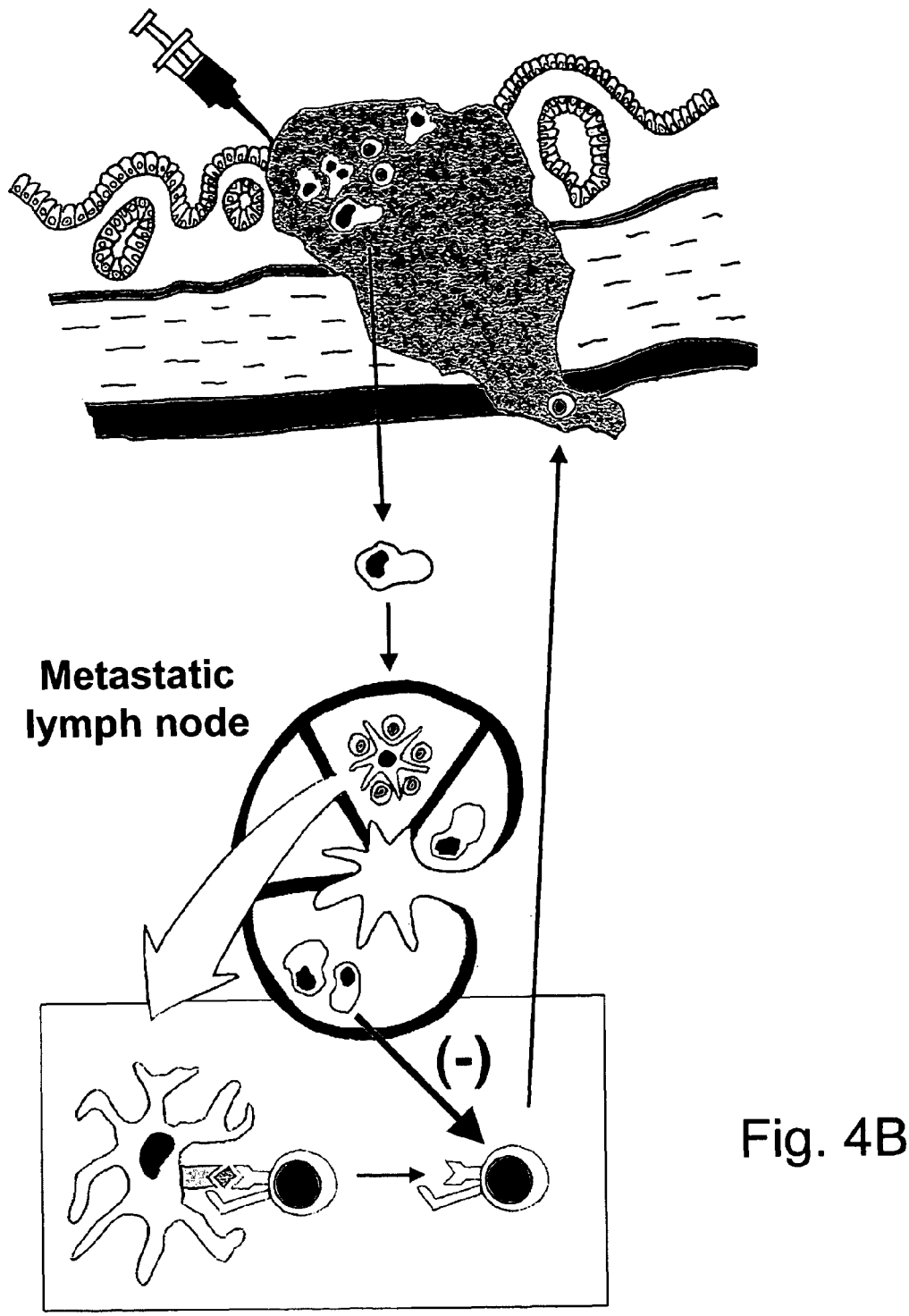

The functional status of the lymphocytes was further characterized in time course proliferation assays using homogenized tumor cell extracts as antigen source (FIG. 2A, B right panels). Stimulation with Patent blue dye did not cause proliferation in any case (data not shown). In all sentinel lymph nodes without metastasis (Dukes B cases), the lymphocytes proliferated in a dose dependent manner against autologous tumor extract (FIG. 2A, right panel). Peak proliferation was regularly seen at day 6 at the highest amount of antigen (Table 1). No antigen dependent proliferation was recognized among lymphocytes from non-sentinel nodes or from TILs. In the Dukes C cases (Table 1, FIG. 2B right panel), where the sentinel nodes contained metastatic cells, none or a very weak proliferative response was identified. To further investigate the functional state of the lymphocytes, T-cells were nonspecifically stimulated with Concanavalin A which by-pass the activation through the T-cell receptor. All PBLs and non-sentinel node lymphocytes responded with strong proliferation as well as sentinel node lymphocytes from the Dukes B patients (FIG. 3A). However, sentinel node lymphocytes from the Dukes C patients did not respond with proliferation against Concanavalin A, nor did the TILs from Duke B or C cases. Stimulation of sentinel node lymphocytes from a Dukes B patient with 100 µg/ml of carcinoembryonic antigen did not result in any proliferative activity (data not shown).

Lymphocytes with specific activity towards autologous tumor extract were selected and put in long term cultures. The stimulated cells consisted of predominantly CD4$^+$ T lymphocytes and they were expanded in the presence of IL-2 and survived in vitro for several weeks.

Cells from the tumors, sentinel and non-sentinel nodes were investigated by FACS after, intracellular staining with cytokeratin-20, a marker of epithelial cancers. We found that permeabilization of cells with saponin permitted detection of a large proportion of cytokeratin-20 positive cells in the tumors (FIG. 3B). Interestingly, we were able to detect a small number of cytokeratin-20 positive cells in a sentinel node with micrometastasis (FIG. 3B, FIG. 2B left panel).

The invention claimed is:
1. A method for treating cancer having a primary tumor in a human patient, comprising
   (a) providing lymphocytes obtained from sentinel lymph nodes from the patient, wherein the sentinel lymph nodes are the first lymph nodes in the lymphatic system that receive lymphatic drainage from the primary tumor area;
   (b) expanding the lymphocytes in vitro, wherein the lymphocytes are stimulated in vitro by addition of a stimulating agent selected from the group consisting of IL-2, IL-12, anti-CD3 antibody, and anti-CD28 antibody and are exposed to recombinant tumor antigen and/or autologous tumor extract, optionally presented with antigen presenting cells selected from B-cells, macrophages, monocytes, dendritic cells, or Langerhans cells; and
   (c) transferring the expanded lymphocytes into the patient.
2. The method of claim 1, wherein the lymphocytes are stimulated with IL-2.
3. The method of claim 1, wherein the lymphocytes are stimulated with anti-CD3 antibody.
4. The method of claim 1, wherein the lymphocytes are stimulated with anti-CD28 antibody.
5. The method of claim 1, wherein the lymphocytes are first exposed to autologous tumor extract and then are stimulated with IL-2.
6. The method of claim 1, wherein the lymphocytes are exposed to recombinant tumor antigen.
7. The method of claim 1, wherein the lymphocytes are exposed to autologous tumor extract.
8. The method of claim 1, wherein the sentinel lymph nodes are free of tumor cells.
9. The method of claim 1, wherein the lymphocytes are separated from the stimulating agent after stimulation.

10. The method of claim 9, wherein the lymphocytes are separated from recombinant tumor antigen and/or autologous tumor extract after exposure.

11. The method of claim 9, wherein after separation, the lymphocytes are restimulated by a further addition of the stimulating agent.

12. The method of claim 11, wherein the further addition of the stimulating agent is made with addition of medium to a culture of the lymphocytes.

13. The method of claim 12, wherein the lymphocytes are restimulated with IL-2.

14. The method of claim 9, wherein after separation, the lymphocytes are restimulated by a further addition of IL-2.

\* \* \* \* \*